United States Patent
Chemello

Patent Number: 6,077,264
Date of Patent: Jun. 20, 2000

[54] INTRAMEDULLARY NAIL FOR THE OSTEOSYNTHESIS OF BONE FRACTURES

[76] Inventor: Antonio Chemello, Via Peraro, 66-36060, Schiavon (VI), Italy

[21] Appl. No.: 09/155,640
[22] PCT Filed: Apr. 3, 1997
[86] PCT No.: PCT/EP97/01675
§ 371 Date: Oct. 2, 1998
§ 102(e) Date: Oct. 2, 1998
[87] PCT Pub. No.: WO97/37606
PCT Pub. Date: Oct. 16, 1997

[30] Foreign Application Priority Data

Apr. 5, 1996 [IT] Italy .................. VI96A0054

[51] Int. Cl.[7] .................... A61B 17/56
[52] U.S. Cl. ............... 606/67; 606/62; 606/64
[58] Field of Search ............ 606/62, 64, 67, 606/60

[56] References Cited

U.S. PATENT DOCUMENTS 4,632,101  12/1986  Freedland .
4,862,883   9/1989  Freeland .
5,057,103  10/1991  Davis .
5,810,820   9/1998  Santori et al. ............ 606/64

FOREIGN PATENT DOCUMENTS 2 289 155  5/1976  France .
2 260 839  6/1974  Germany .
  453 570  6/1968  Switzerland .

*Primary Examiner*—Michael Buiz
*Assistant Examiner*—Julian W. Woo
*Attorney, Agent, or Firm*—Watson Cole Grindle Watson, P.L.L.C.

[57] ABSTRACT

The invention discloses an intramedullary nail to be used in orthopedics comprising: a tubular body having inside at least one anchoring device; a maneuvering element and a drilled bushing at the top end of said nail wherein said tubular body, substantially cylindrical, has the top end not cylindrically shaped. The anchoring device is provided with two or more longitudinal cavities shaped for housing a hook with arched tip pointed towards the outer side of the tube and movable with respect to the housing cavity during the sliding of the anchoring device with respect to the tube. The maneuvering element, housed inside the tubular body, operates the longitudinal sliding in the two opposite directions of said anchoring device. The drilled bushing slides without rotation with the non-cylindrical top end of said tubular body and has at least one arched lip for the contact with the bone.

20 Claims, 9 Drawing Sheets

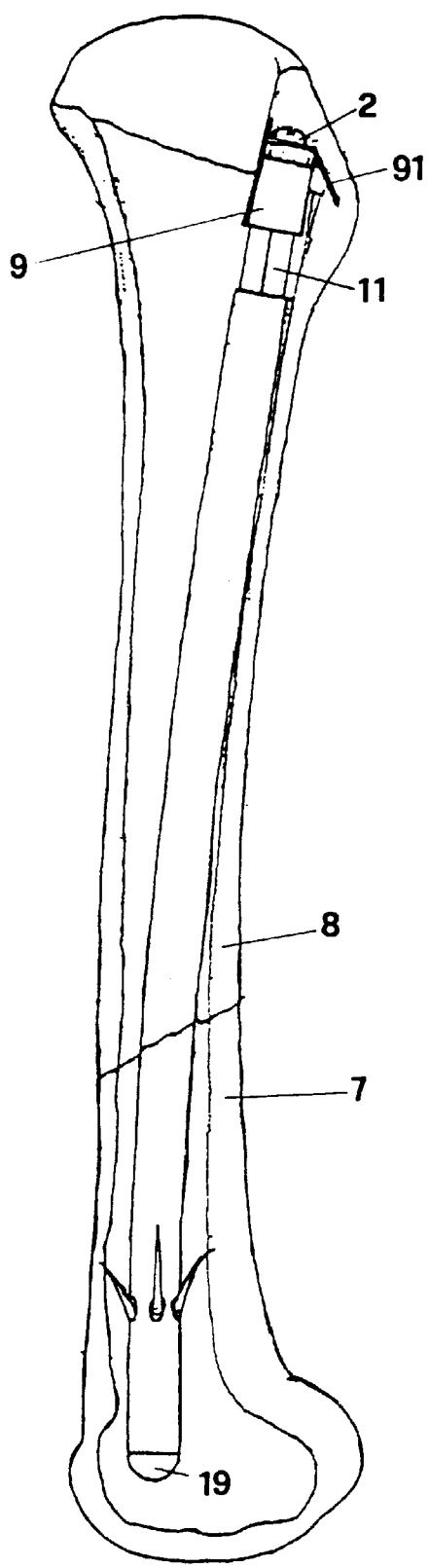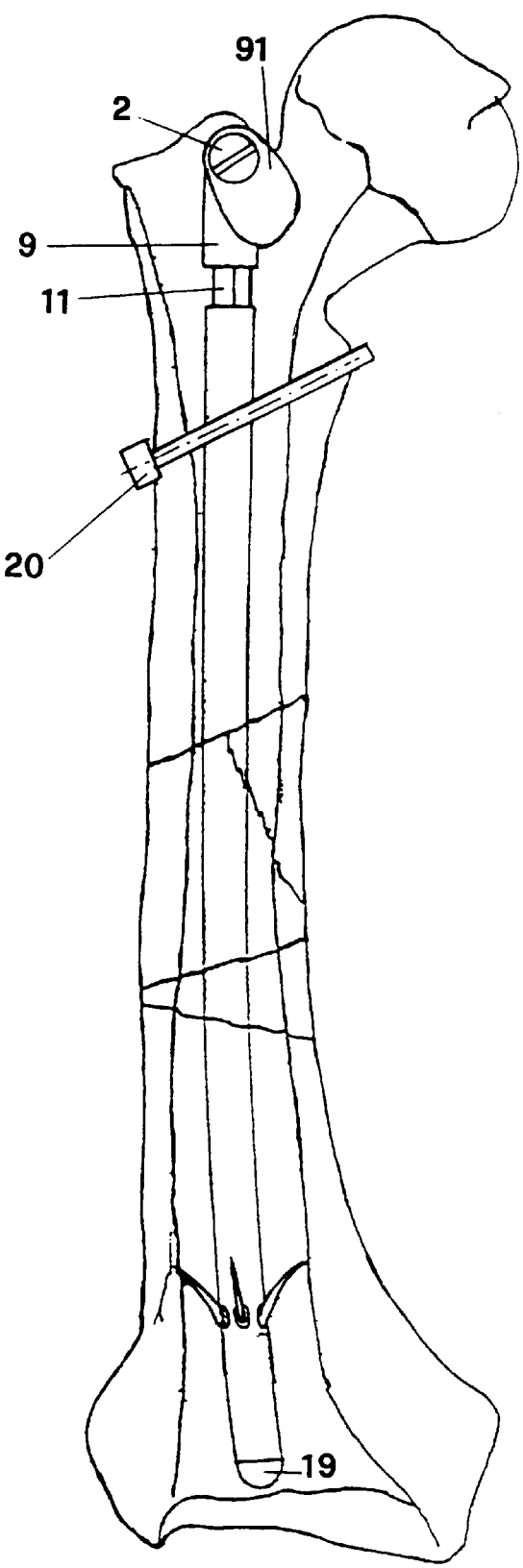
FIG.2
FIG.4a

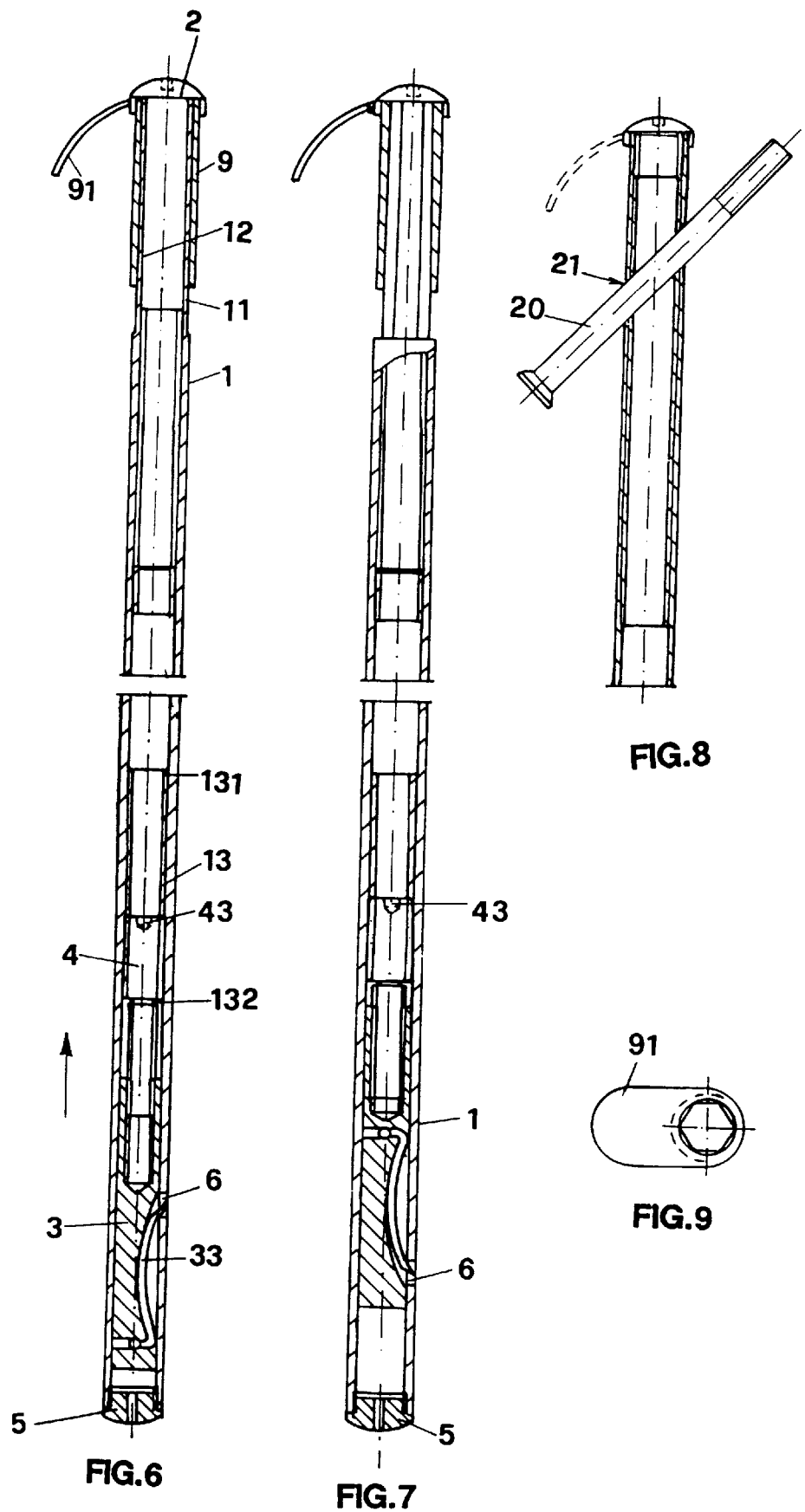

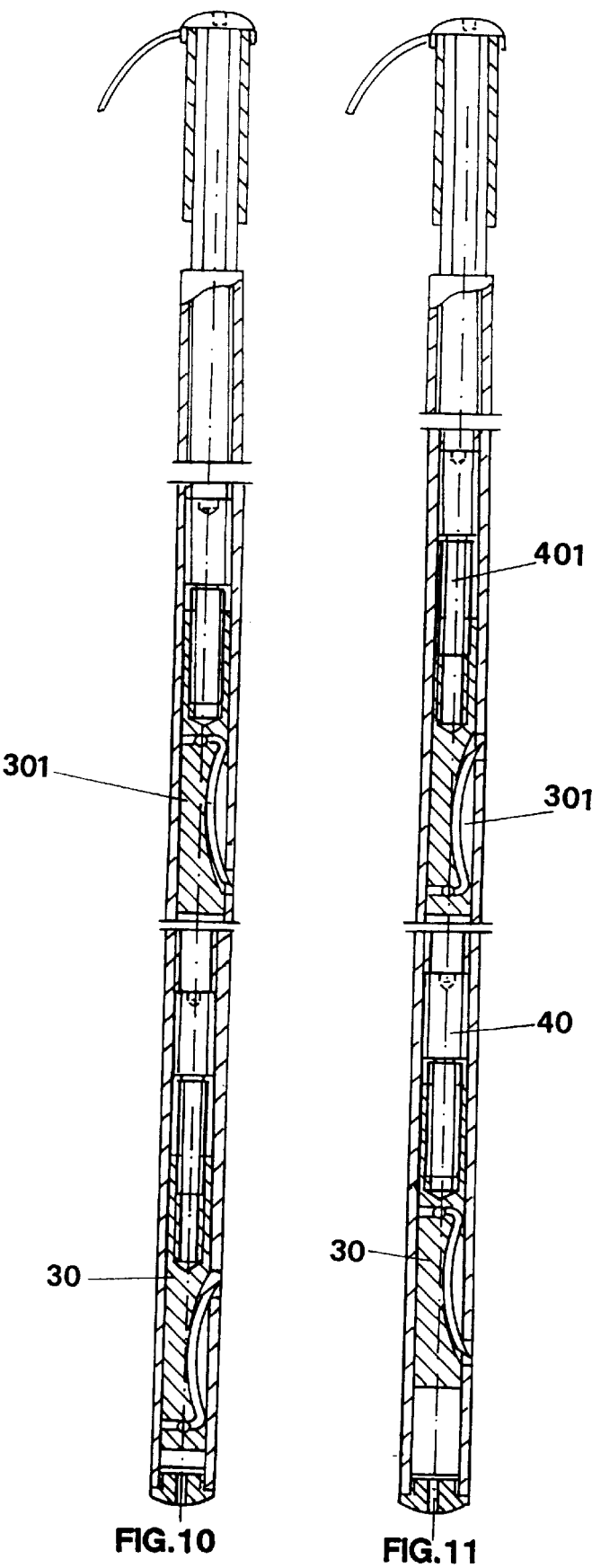

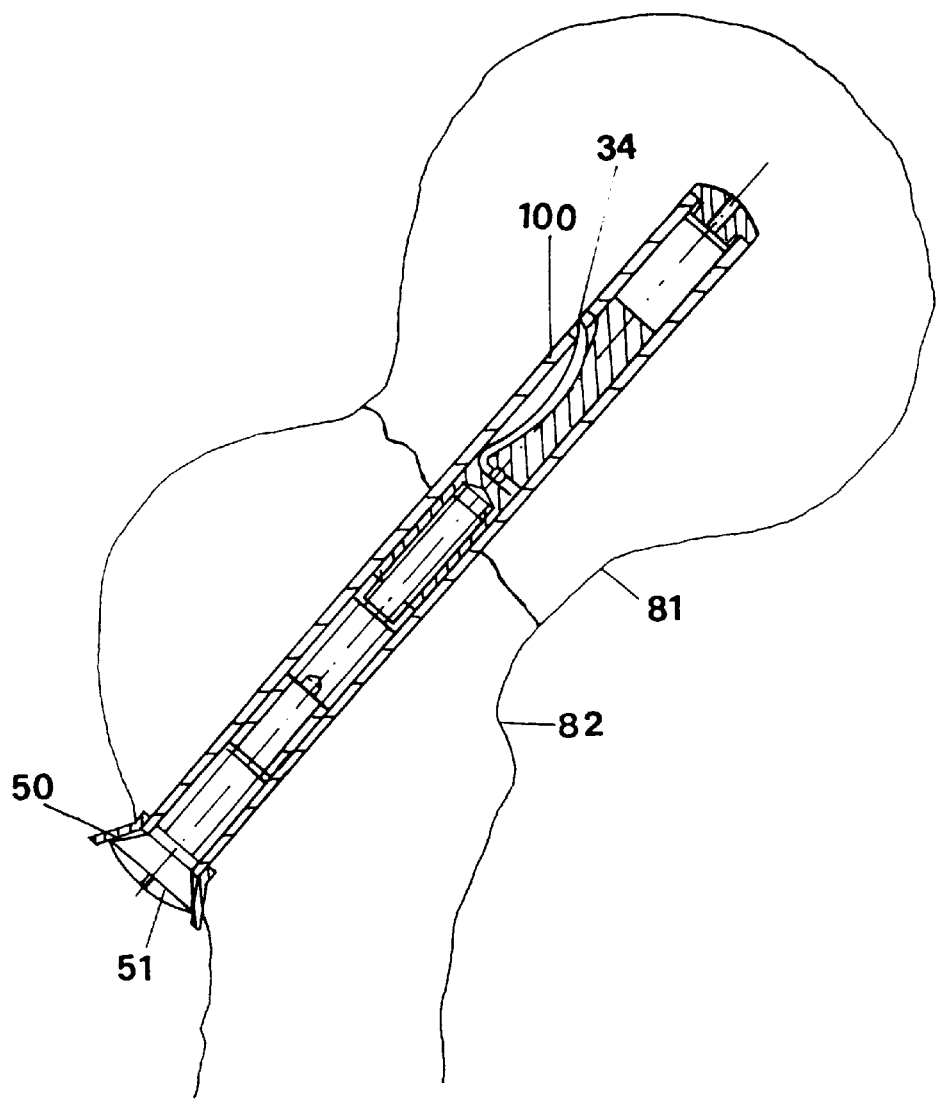
FIG.13
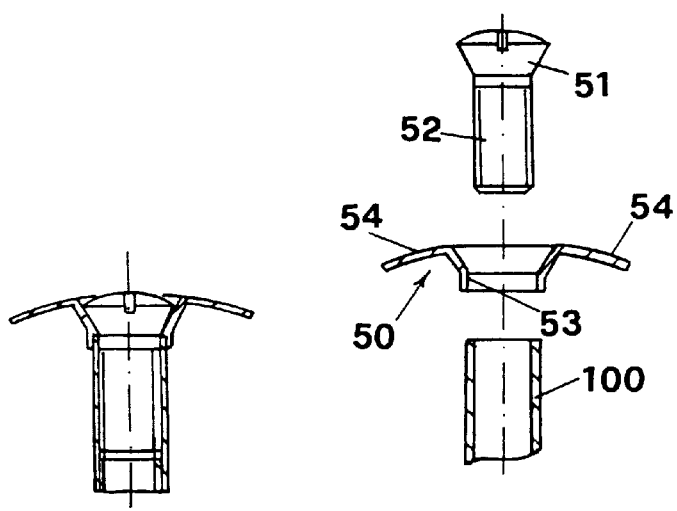
FIG.15   FIG.14

INTRAMEDULLARY NAIL FOR THE OSTEOSYNTHESIS OF BONE FRACTURES

BACKGROUND OF THE INVENTION

The invention concerns a tubular intramedullary nail to be used in orthopedics for the reduction of bone fractures.

It is well known that in orthopedic surgery tubular metal rods called "nails" to be inserted in the fractured bone after drilling the medullary canal of the bone itself are used in most cases for the treatment of fractures, especially fractures of the long bones. In order to avoid the rotation of the fragments and their shortening in multifragmented fractures. The known technique requires the intersection of said nail by means of anchoring screws that pass through apposite holes. The insertion of the nail and, above all, the distal locking of the nail itself on the fragments of the fractured bone are rather complex operations, due also to the fact that it is often difficult to center the screws to be inserted on the nail holes.

Another drawback connected with the known technique is represented by the fact that during the fracture consolidation time, the nail, locked as it is through transverse screws, actually prevents any relative movement of the fractured bone fragments in the longitudinal direction. This is obviously a limitation of the known technique, in fact, since a moderate physiological absorption of the fractured parts takes usually place, a dynamic compaction is practically impossible. Therefore, the impossibility to bring the two bone fragments under dynamic load near each other prolongates the fracture consolidation time.

The U.S. Pat. No. 5,057,103 discloses a nail for long bones comprising a tubular body having in his interior an anchoring device which holds the lower part of the fractured bone permitting the compression of the parts of the fractured bone, but said kind of nail, per se, does not avoid the rotation and the shearing of said fractured parts.

SUMMARY OF THE INVENTION

The invention aims at eliminating the above mentioned drawbacks. One of the aims of the invention is the implementation of a new nail that should prevent the bone fragments from rotating, with no need to lock the nail itself by means of a series of transverse screws.

A further aim is the implementation of a nail provided with all the devices necessary to anchor the fragments. Though fixed to the fractured bone, said nail should not prevent the dynamic compaction of the fragments themselves when the limb is subjected to axial dynamic load, for example when the body weight rests on the limb itself.

Another goal of the invention is the implementation of a nail that can be easily removed from the bone inner cavity when this is necessary for any reason whatsoever.

The aims described above and others that will be better described herebelow are achieved through the implementation of an intramedullary nail.

To advantage, according to the invention the anchoring device positioned inside the intramedullary nail locks the distal fragment part by means of two or more hooks that come out of the intramedullary nail during the operation of the device. The intramedullary nail can be provided with one or more anchoring devices, for example two, depending on the type of fracture that must be treated.

As far as simple fractures (transverse, oblique, etc.) are concerned, only one anchoring device can be used inside the intramedullary nail and its action will involve the lower part of the fragment. The compaction of the two fragments is achieved through the action of the screw that rests against the bushing on the proximal end of the intramedullary nail. Said bushing, the body of which is coupled with the non-cylindrical part of the nail positioned inside the bone, rests on the outer surface of the bone by means of one or more lips, thus preventing the rotation of the two fragments and at the same time bringing the lower part of the fragment near the upper part, until obtaining their compaction. As will be better illustrated below, the fact that the bushing can slide with respect to the end of the intramedullary nail makes it possible to obtain the compaction of the fragment even during the fracture consolidation period, since the axial dynamic load of the limb pushes the lower fragment agaĩnt the upper fragment, this being possible thanks to the relative movement between the bushing and the upper end of the intramedullary nail.

BRIEF DESCRIPTION OF THE DRAWINGS

Further characteristics and details of the invention will be better highlighted in the following description of the invention in question, illustrated in the attached drawings, wherein:

FIG. 2 shows the thighbone of FIG. 1 after compaction;

FIG. 4a shows the thighbone of FIG. 3 and 4 compacted with the nail of FIG. 2 and stabilized by means of a transverse screw;

FIG. 6 shows a section of the nail object of the invention comprising one anchoring device only;

FIG. 7 is a variant of FIG. 6, in which the anchoring device is positioned so that the coming out of the hook tips is reversed with respect to that shown in FIG. 6;

FIG. 8 shows a section of the nail object of the invention associated with a transverse screw to be used for multifragmented diaphyseal fractures, as shown in FIG. 4a;

FIG. 9 is a top view of the detail of the lip with which the nail bushing is provided;

FIGS. 10 and 11 show the sections of two nails according to the invention, each one being provided with two anchoring devices directed convergently and divergently, respectively;

FIG. 13 shows the nail object of the invention used for basal neck fractures;

FIGS. 14 and 15 show an exploded view and a section, respectively, of an application of the bushing and screw associated to the nail object of the invention;

DESCRIPTION OF THE INVENTION

Figure 5:
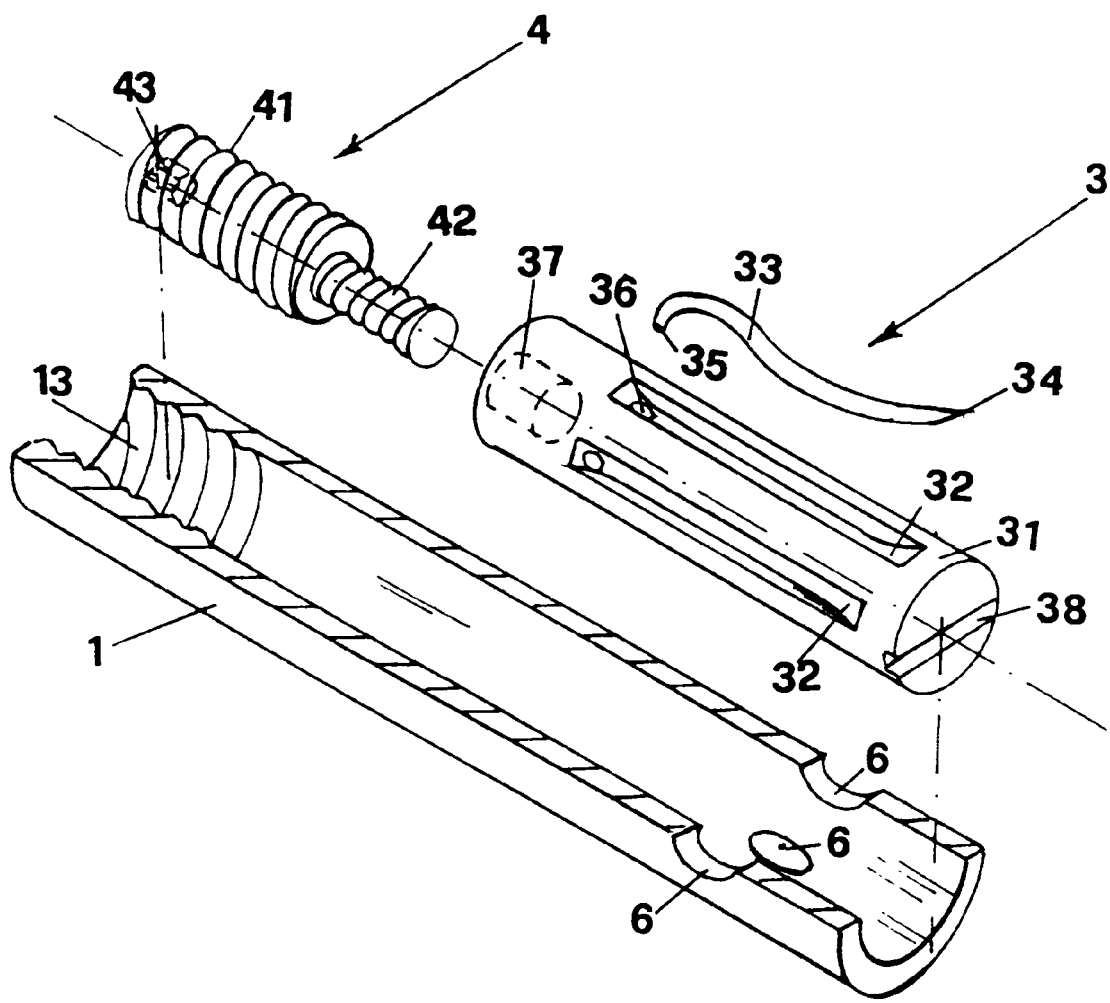
FIG. 5 is an exploded view of the anchoring device and of the maneuvering device with which the intramedullary nail object of the invention is provided.

With reference to the above mentioned figures, particularly to FIGS. 5 and 6, it can be observed that the nail object of the invention, a section of which is shown in FIG. 6, comprises a tubular body, indicated as a whole by 1, the end 11 of which has external octagonal shape obtained from the outer diameter of the tubular body 1 through machining. The inside of said tube 1 is provided with two threads, one in correspondence with the external octagonal area 11, said thread being indicated by 12 and used, as will be explained below, for screwing the screw 2. The other thread is situated in the inner body of the tube 1 and is indicated by 13. This thread occupies only one part of the tubular body, and precisely the area included between the references from 131 to 132, on which the anchoring device 3 will be screwed. Said anchoring device, indicated as a whole by 3 and visible in detail in FIG. 5, comprises a cylinder 31 provided with four longitudinal cavities 32, only two of which can be seen in the exploded view of FIG. 5, each of said four longitudinal cavities being suitable for receiving a hook indicated by 33, said hook having arched shaped and being provided with a tip 34 and an opposite end with substantially round section 35 that fits into a hole 36 made on the basis of the longitudinal cavity 32. The cylindrical body 31 comprises also a threaded housing 37 suitable for receiving the element 4 that will ensure the longitudinal movement of the anchoring device in both directions. On its opposite end the cylindrical body 31 is provided with a slot for a screwdriver indicated by 38. The anchoring device cooperates with a device, indicated as a whole by 4, which, as can be seen in FIG. 5, comprises a threaded rod with double diameter 41 and 42, respectively, where, in the example, the thread 41 of the longer diameter is a right thread and the thread 42 of the shorter diameter is a left thread. The thread 41 screws on the inner thread 13 belonging to the tubular body 1, while the thread 42 screws on the threaded hole 37 belonging to the anchoring device 3.

The element 4 is directly coupled with the anchoring device 3 complete with the hooks 33 and inserted into the tube 1. As shown in FIGS. 6 and 7, the lower end opposite the non-cylindrical length of the tube 1 is closed with a threaded plug 5. This plug also serves to stop the sliding of the anchoring device during its, in fact it acts as end of stroke. With reference to either FIG. 6 and FIG. 7, when the tips 34 of the hooks 33 are near the slots 6 provided on the surface of the tubular body 1, the rotation of the anchoring device 3, obtained for example through the insertion of the tip of a screwdriver into the slot 38 of the tubular body 31, will make it possible to direct the anchoring device correctly, making the tips 34 of each hook come out through the slots 6.

It is clear that a successive operation with a manual tool not represented in the drawings, for example with an hexagon spanner, on the hexagon 43 of the element 4, will ensure the rotation of said manoeuvring element and therefore the travel in either directions, according to the rotation direction of said element, of the anchoring device 3.

Figure 1:
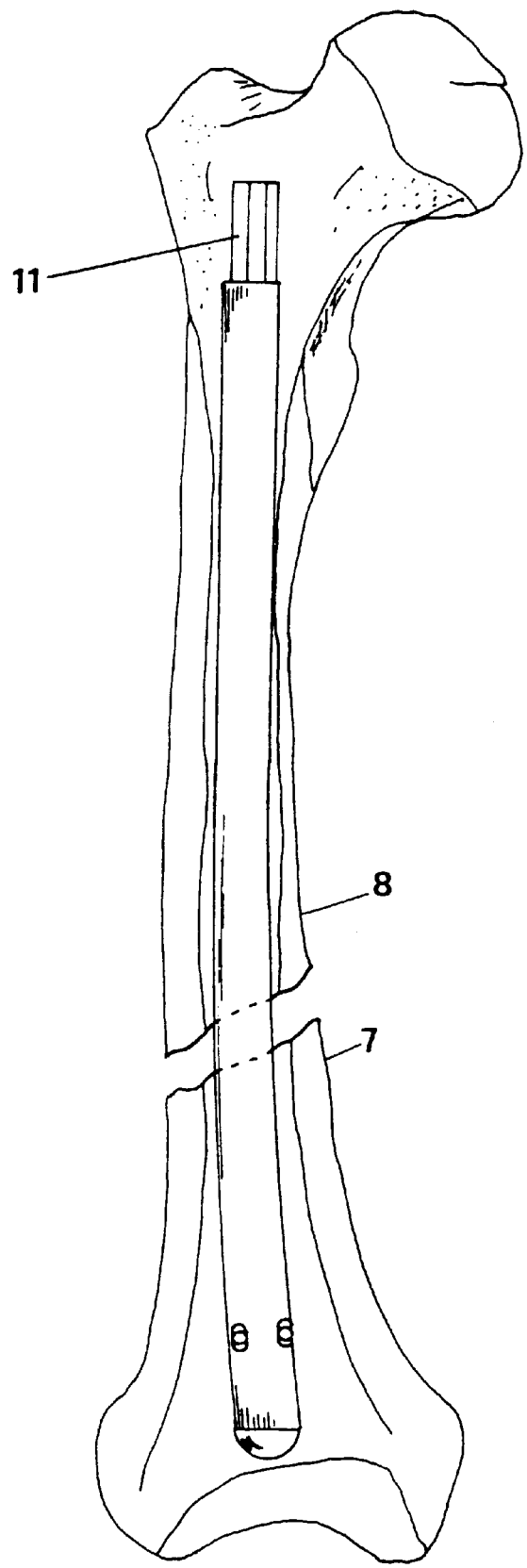
FIG. 1 shows the application of the nail object of the invention to a thighbone with simple fracture.

With reference to FIG. 6, when the element 4 moves in the direction of the arrow, the anchoring device is pulled upwards and consequently the hooks 33 come out of the slots 6 as illustrated in FIG. 2, which shows the application of the nail object of the invention to a thighbone with simple fracture. In this case the hooks 33 of the nail extend from the slots 6 upwards, the type of nail being that shown in section in FIG. 6. In the case of a simple fracture, the extension of the hooks 33 towards the outside of the nail and therefore in anchoring position with respect to the bone takes place in the distal part of the bone and before the compaction of the two fragments. In fact, the sequence of the operations to be performed with the nail object of the invention basically consists in the introduction of the nail in the medullary canal of the bone prepared in advance. Successively the element is operated, so that the anchoring device locks the distal fragment. The two fragments indicated by 7 and 8 in FIG. 1 are then brought near each other through the pressure exerted by the head of the screw 2 onto the bushing 9, which is provided with a hole having the same shape as the end 11 of the tubular body 1, in this case octagonal, and the body of which is housed inside the bone. As a consequence of this, the bushing 9 can only slide longitudinally downwards, but cannot rotate. If the bushing slides downwards, the lip 91 integral with the upper part of the bushing 9 comes to rest on the outer part of the bone 8. In this way, any screwing of the screw 2 can only move the whole tubular body 1 of the nail upwards and therefore compact the two fragments 7 and 8, as shown in FIG. 2. Therefore, in the case of a simple fracture, as shown in FIGS. 1 and 2, it is sufficient to use a single anchoring device 3 inserted in the nail object of the invention, since said device ensures the locking of the fragment 7, while the locking of the fragment 8 in rotation is due to the external action of the lip 91 belonging to the bushing 9.

During the patient's convalescence, the axial dynamic load to which the two fragments are subjected improves their compaction, said compaction being facilitated by the presence of the nail object of the invention, in fact the whole nail can lift, since it can slide on the groove of the bushing 9.

Figure 3:
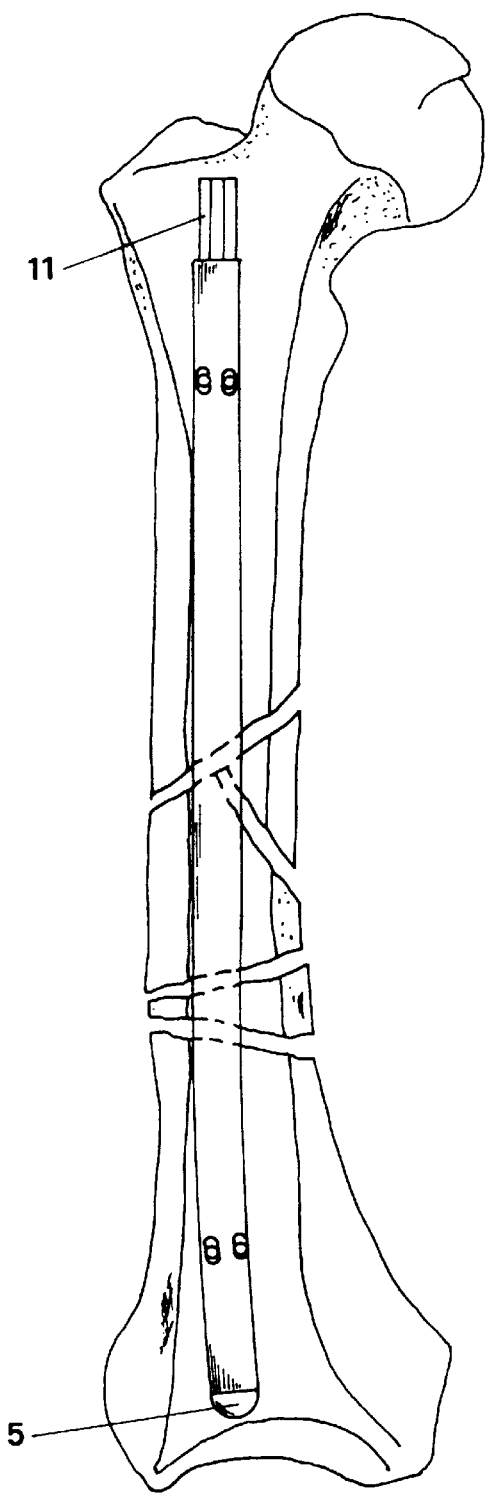
FIG. 3 shows the nail object of the invention provided with two anchoring devices in a thighbone with a multifragmented fracture before compaction.
Figure 4:
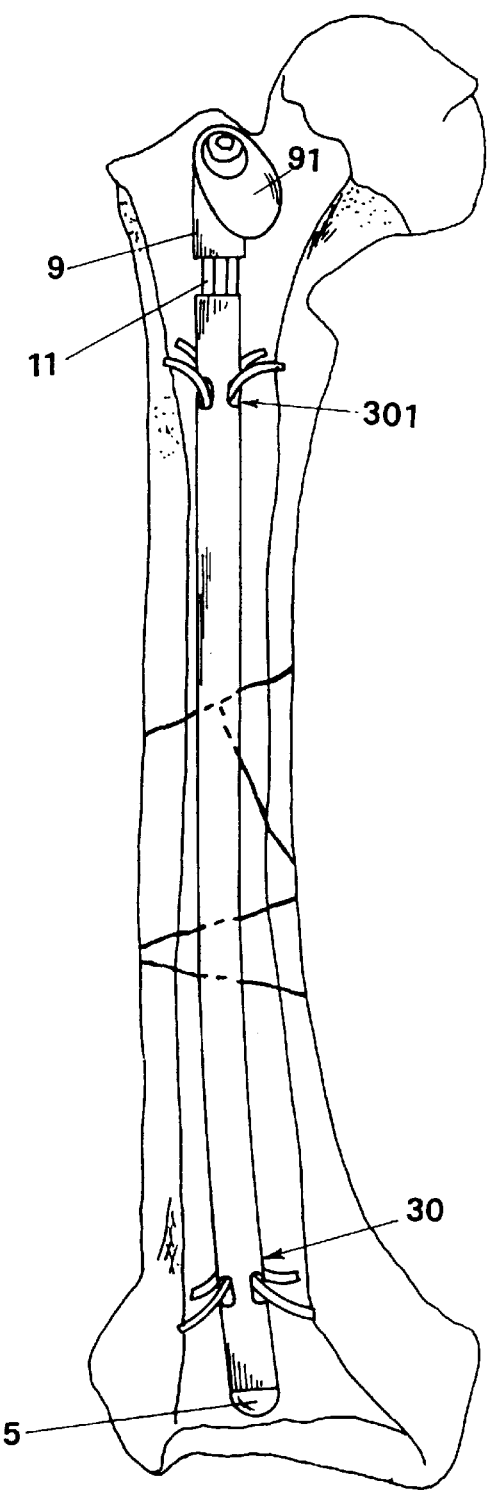
FIG. 4 shows the thighbone of FIG. 3 after compaction.

In the case of multifragmented fractures, as shown in FIGS. 3 and 4, the nail must be provided with at least two anchoring devices 3. More specifically, it can be observed that the nail object of the invention used for the fracture shown in FIGS. 3 and 4 is the nail a section of which is shown in FIG. 11, where two anchoring devices 30 and 301 opposite to each other and operated by the respective elements 40 and 401 are provided. FIG. 10 shows a further variant, in which the nail is also provided with two anchoring devices 30 and 301, which however are directed convergently and not divergently as in FIG. 11. The advantage ensured by the double locking that can be obtained for multifragmented fractures, as already said, is evident. FIG. 3 shows the multifragmented bone with the nail with double anchoring device. Obviously, the first device 30 must be firstly operated, then the bone fragments are to be compacted and then the second extension or locking of the second anchoring device must be performed. After this, the nail can be definitively fixed with the bushing 9, properly directing the lip 91.

If, for safety reasons, it is necessary to carry out the proximal locking of the nail object of the invention with a transverse screw 20, this can be easily made, since the nail object of the invention is also provided with a transverse hole 21 for the insertion of said screw, as shown in FIG. 4a and in section in FIG. 8.

Figures 12, 16:
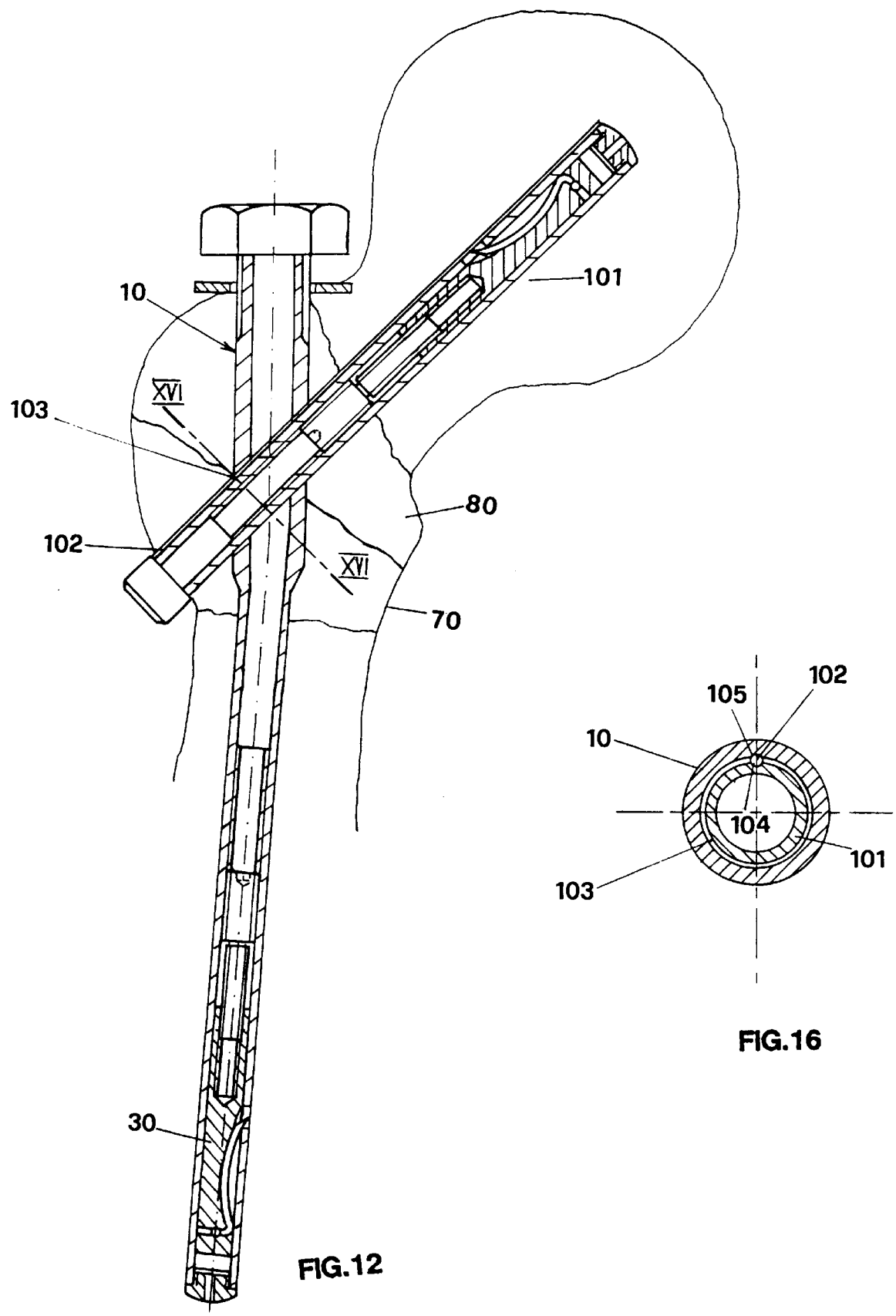
FIG. 12 shows a particular execution of the nail object of the invention used for per-subtrochanteric fractures of the thighbone.
FIG. 16 shows a section of the transverse nail of FIG. 12 according to the line XVI—XVI.

In the case of fractures of the thighbone, as those shown in FIG. 12, where a per-subtrochanteric fracture is shown, two nails according to the invention, indicated by 10 and 101, respectively, can be inserted in the thighbone. In this case the nail 10 is slightly bent to follow the shape of the bone and is provided with one anchoring device 30 only, for the distal locking. A further nail 101, provided with only one anchoring device 30 as well, is used to replace the traditional cephalic screw, so that the anchorage of the device through the hooks on a bone part that is far from the fracture is ensured. It must be observed that the use of the nail 101 prevents the rotation of the proximal part of the fracture. It must also be observed that the rotation between the nail 101 and the nail 10 is prevented by the presence of a rod 102 housed in a lowered longitudinal impression 104 present on the outer surface of the nail 101, which corresponds to an equal cavity 105 on the hole 103 belonging to the nail 10. This can be seen in FIG. 16, which shows the section of the nail 101 according to the line XVI—XVI.

Figure 12A:
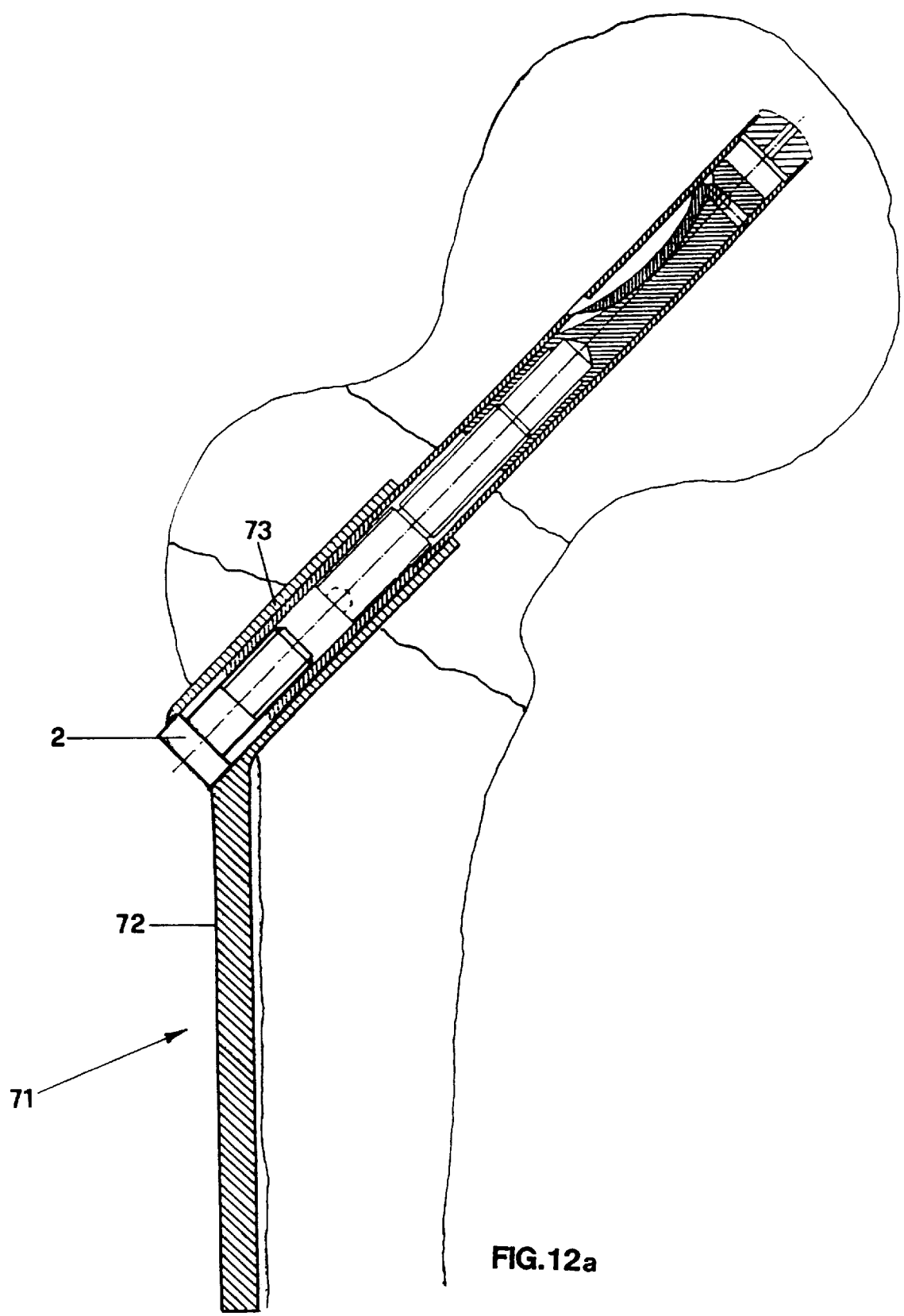
FIG. 12a shows a particular execution of the nail used for the same fractures illustrated in FIG. 12.

FIG. 12a shows the nail object of the invention with an angular plate 71 to replace the bushing. This plate presents a substantially flat longitudinal rod 72 that rests on the thighbone and is connected with a tubular body 73 that couples with the non-cylindrical part of the nail and on which the head of the screw 2 rests to achieve the compaction of the fracture.

FIG. 13 shows the introduction of the nail object of the invention in a basal neck fracture. In such a case, it is important that in the part 81 the anchorage with the nail hooks takes place in the thighbone part with longer diameter, therefore it is necessary to use a nail having the hook tips directed towards the terminal part of the nail itself, that is, a nail of the type shown in FIG. 7, while in the operation to which FIG. 12 refers a nail of the type shown in FIG. 6 is used. FIGS. 14 and 15 show a special bushing shaped like an expansion washer, indicated by 50 and having two symmetrical lips 54 and a non-cylindrical hole 53, said bushing resting against the surface of the fragment 82 through the pressure of the head 51 of the screw 52 that screws on the tubular element of the nail 100.

What is claimed is:

1. Intramedullary nail to be used in orthopedics for insertion into a bone comprising:
   a tubular body having an interior and including at least one anchoring device slidably moveable within the interior thereof;
   a maneuvering element for said anchoring device housed within the tubular body; and
   a drilled bushing at the top end of said nail;
   wherein said tubular body is substantially cylindrical and has a parallelopiped shaped top end and a threaded interior portion at said top end;
   wherein said at least one anchoring device has a substantially cylindrical body formed with an cylindrical surface and having two or more longitudinal cavities formed therein, and the body has a plurality of slots, one each, corresponding to each of said cavities, a hook having an arched tip located in each cavity, each of said cavities being shaped for housing a corresponding one of the hooks with the arched tip pointed towards the exterior surface of the tube and facing a corresponding slot positioned on the cylindrical surface of said tubular body, each hook being movable with respect to the cavity into and out of the corresponding slot during the slidable movement of the anchoring device with respect to the tubular body;
   wherein said maneuvering element, housed within the tubular body is operated for, longitudinal sliding in two opposite directions of said at least one anchoring device, causing each hook to extend through the corresponding slot exterior of the tubular body;
   and wherein said drilled bushing slides without rotation with respect to the top end of said tubular body and has at least one arched lip for the contact with the bone in which said nail is inserted, a threaded screw having a head resting on the bushing, said bushing cooperating with the screw and threadably engaging the threadable interior portion of the tubular body.

2. The intramedullary nail according to claim 1, wherein each hook has a proximal end opposite the tip and each cavity has a radial hole for receiving the proximate end therein, and during movement of each hook through the corresponding slot each hook lifts from the cavity while the proximal end remains located in the radial hole.

3. The intramedullary nail according to claim 1, wherein the maneuvering element comprises a threaded rod having first and second oppositely threaded portions, the first portion having a diameter larger than the second portion, the second threaded portion for threadably engaging a threaded hole at the end of the anchoring device, the first threaded portion for threadably engaging the threaded portion of the tubular body; and an axial opening for receiving a maneuvering spanner.

4. The intramedullary nail according to claim 1 wherein the body has a transverse hole.

5. The intramedullary nail according to claim 1 including at least two of said anchoring devices being positioned in opposite directions, so that the respective hooks extend in opposite directions with respect to one another.

6. The intramedullary nail according to claim 1 wherein the tubular body has a lower end with an opening therein, and wherein a closing plug is located in said opening in lower end.

7. The intramedullary nail according to claim 1 wherein the bushing comprises an expansion washer formed with two symmetrical lips for resting on the bone.

8. The intramedullary nail according to claim 1 wherein the bushing comprises a plate in the form of a substantially flat longitudinal rod secured by the screw to the top end of the tubular body.

9. The intramedullary nail according to claim 1 including a second nail, and having a transverse hole through which said second nail is inserted, and a rod located in longitudinal impressions in a surface of the hole and a surface of said nail.

10. The intramedullary nail according to claim 9 including another anchoring device positioned in an opposite direction to the first mentioned anchoring device, so that the respective hooks extend from the tubular body in opposite directions.

11. The intramedullary nail according to claim 9 including a closing plug at the distal end.

12. The intramedullary nail according to claim 1 wherein the bushing comprises a flat plate.

13. The intramedullary nail according to claim 1 wherein the bushing comprises a washer with two symmetrical lips.

14. An intramedullary orthopedics nail comprising:
   a tubular body having an interior cavity, proximal and distal ends and at least two slots near the distal end;
   at least one anchoring device within the interior cavity in the form of a substantially cylindrical body axially slidable in the interior cavity near the slots in the distal end and having at least two longitudinal cavities each one of said longitudinal cavities being associated with a corresponding one of said slots;
   an arc shaped hook for each longitudinal cavity, each having a pointed tip end engaging the corresponding slot and extending in a direction outwardly of the tubular body and, said hook being movable inwardly and outwardly of the tubular body with movement of the cylindrical body within the longitudinal cavity, each hook has a radially extending proximal end and the cylindrical body has a corresponding radial opening at the proximal end of the cavity for receiving the end of the hook in bearing relationship;
   a rotatable maneuvering element, axially located within the tubular body secured to a proximal end of the anchoring device operative for sliding the body in opposite directions axially within the longitudinal cavity towards and away from the distal end, causing respective extension and withdrawal of the hooks through the slots in the tubular body;

a bushing secured to a proximal end of the maneuvering element at the corresponding end of the tubular body being slidable thereon and secured thereto without rotation, said bushing including at least one outwardly extending arched lip at said proximal end.

15. The intramedullary nail according to claim 14 wherein the maneuvering element comprises a rod having a threaded portion for engaging a corresponding threaded portion within the tubular body and a non-cylindrical proximal end.

16. The intramedullary nail according to claim 15 wherein the tubular cavity has a selected diameter and the maneuvering element has an unthreaded portion slidable therein.

17. The intramedullary nail according to claim 15 wherein the maneuvering element has a threaded distal end with a reduced diameter for engaging a corresponding threaded opening in the cylindrical body.

18. The intramedullary nail according to claim 14 having a transverse hole and a screw for locking the maneuvering element.

19. The intramedullary nail according to claim 14 wherein the top end of the body coupled with the drilled bushing has a parallelepiped shape.

20. An intramedullary orthopedics nail comprising:

a tubular body having an interior cavity, proximal and distal ends and at least two slots near the distal end;

at least one anchoring device within the interior cavity in the form of a substantially cylindrical body axially slidable in the interior cavity near the slots in the distal end and having at least two longitudinal cavities, each one of said longitudinal cavities being associated with a corresponding one of said slots;

an arc shaped hook for each longitudinal cavity, each having a pointed tip end engaging the corresponding slot and extending in a direction outwardly of the tubular body and, said hook being movable inwardly and outwardly of the tubular body with movement of the cylindrical body within the longitudinal cavity, each hook having a proximal end and the cylindrical body has a corresponding bearing surface at the proximal end of the cavity for receiving the end of the hook in bearing relationship;

a rotatable maneuvering element, axially located within the tubular body secured to a proximal end of the anchoring device operative for sliding the body in opposite directions axially within the longitudinal cavity towards and away from the distal end, causing respective extension and withdrawal of the hooks through the slots in the tubular body;

a bushing secured to a proximal end of the maneuvering element at the corresponding end of the tubular body being slidable thereon and secured thereto without rotation, said bushing including at least one outwardly extending arched lip at said proximal end.

* * * * *